(12) United States Patent
Lee et al.

(10) Patent No.: US 12,336,789 B2
(45) Date of Patent: Jun. 24, 2025

(54) SMALL BLOOD VISCOSITY MEASUREMENT KIT AND CARTRIDGE THEREFOR

(71) Applicant: Biorheologics Co., Ltd., Jeonju-si (KR)

(72) Inventors: Donghwan Lee, Jeonju-si (KR); Euiho Lee, Yeosu-si (KR); Uiyun Lee, Jeonju-si (KR)

(73) Assignee: Biorheologics Co., Ltd., Jeonju-si (KR)

( * ) Notice: Subject to any disclaimer, the term of this patent is extended or adjusted under 35 U.S.C. 154(b) by 749 days.

(21) Appl. No.: 17/628,441

(22) PCT Filed: Jul. 6, 2020

(86) PCT No.: PCT/KR2020/008802
§ 371 (c)(1),
(2) Date: Jan. 19, 2022

(87) PCT Pub. No.: WO2021/015447
PCT Pub. Date: Jan. 28, 2021

(65) Prior Publication Data
US 2022/0257123 A1    Aug. 18, 2022

(30) Foreign Application Priority Data
Jul. 19, 2019    (KR) .................. 10-2019-0087898

(51) Int. Cl.
*A61B 5/02*       (2006.01)
*A61B 5/155*      (2006.01)

(52) U.S. Cl.
CPC .......... *A61B 5/02035* (2013.01); *A61B 5/155* (2013.01)

(58) Field of Classification Search
CPC ............... A61B 5/02035; A61B 5/155; G01N 2011/006; G01N 11/04; G01N 33/49;
(Continued)

(56) References Cited

U.S. PATENT DOCUMENTS

2011/0100100 A1* 5/2011 Strand ............ G01N 27/44704
                                                    210/85

FOREIGN PATENT DOCUMENTS

JP       H07-119685 B2     12/1995
KR     10-2002-0063571 A    8/2002
(Continued)

OTHER PUBLICATIONS

Machine Translation of KR 101476923, Patent Translate, pp. 1-30, printed on Oct. 9, 2024 (Year: 2014).*
(Continued)

*Primary Examiner* — Daniel L Cerioni
*Assistant Examiner* — Om Patel
(74) *Attorney, Agent, or Firm* — Bridgeway IP Law Group, PLLC; Sang Ho Lee; Hyun Woo Shin

(57) ABSTRACT

Provided is a small blood viscosity measurement kit and a cartridge therefor. The small blood viscosity measurement kit configured to measure a blood viscosity includes: a kit body; two blood pipes disposed symmetrically on two sides of the kit body, wherein an upper side of each of the two blood pipes is open and configured to receive blood injected thereinto; and a fine channel connected to a lower side of the each of the two blood pipes. When blood is injected into one of the two blood pipes, the blood is supplied to the other of the two blood pipes through the fine channel. In addition, there is provided a small blood viscosity measurement kit cartridge, in which a plurality of small blood viscosity measurement kits are stored and kept, and the small blood viscosity measurement kit cartridge automatically supplies the small blood viscosity measurement kits.

12 Claims, 9 Drawing Sheets

(58) Field of Classification Search
CPC .. B01L 3/00; B01L 3/5027; B01L 2200/0689; B01L 2300/088
See application file for complete search history.

(56) References Cited

FOREIGN PATENT DOCUMENTS

| | | | |
|---|---|---|---|
| KR | 10-1375752 B1 | 3/2014 | |
| KR | 101375752 | * 3/2014 | |
| KR | 10-1476923 B1 | 12/2014 | |
| KR | 101476923 | * 12/2014 | |
| KR | 10-1701334 B1 | 2/2017 | |
| WO | WO-0136936 A1 * | 5/2001 | ......... A61B 5/02035 |

OTHER PUBLICATIONS

Machine Translation of KR 101375752, Patent Translate, pp. 1-20, printed on Oct. 9, 2024 (Year: 2014).*

* cited by examiner

SMALL BLOOD VISCOSITY MEASUREMENT KIT AND CARTRIDGE THEREFOR

TECHNICAL FIELD

The present invention relates to a small blood viscosity measurement kit and a cartridge therefor, and more particularly, to relates to a small blood viscosity measurement kit and a cartridge therefor in which a structure is miniaturized and integrated, a manufacturing process is simple, a manufacturing cost is low, and it is easy to be used in an automated device for blood viscosity measurement to solve limitations of conventional blood viscosity measurement devices used for the blood viscosity measurement.

BACKGROUND

The viscosity of blood is a physical property indicating a flow resistance due to a flow of blood in the blood vessel, and can be specifically divided into whole blood viscosity and plasma viscosity. An abnormal increase in blood viscosity causes an increase in shear stress and flow resistance acting on the inner wall of the blood vessel, thereby significantly increasing a risk of acute cardiovascular disease and microvascular disease. In addition, plasma viscosity is used for diagnosing inflammatory conditions in the body, but is also one of the main causes of increasing whole blood viscosity.

Whole blood viscosity illustrates flow characteristics in which the viscosity is continuously changed according to the systolic and diastolic phases of the heart. The reason is that due to complex effects of red blood cells and plasma proteins in whole blood, the viscosity decreases when the blood flows at a high speed (when the shear rate is high), and conversely, the viscosity increases when the blood flows at a slow speed (when the shear rate is low). A fluid having such flow characteristics is called a non-Newtonian fluid. In order to appropriately understand the non-Newtonian flow characteristics of blood, it is necessary to accurately measure the whole blood viscosity for a total shear rate (for example, 1 to 1,000 $s^{-1}$).

As a blood viscosity measurement method that is currently commercialized and widely used in clinical practice, a technique of measuring the blood viscosity by using a U-shaped double vertical tube/single capillary viscometer is representative.

To briefly summarize the technique, it is a method of measuring the blood viscosity by filling two left and right vertical tubes with blood at different heights, and measuring a speed at which the blood heights are naturally equal to each other by gravity in real time.

Such a U-shaped double vertical tube/single capillary viscometer uses a disposable U-shaped tube, so it does not require washing, it is easy to be used in clinical practice, there is no risk of infection, it is possible to measure the viscosity measurement in a range of a shear rate of 1~1000 $s^{-1}$, and it is possible to measure the whole blood viscosity and the plasma viscosity.

The U-shaped double vertical tube/single capillary viscometer has the following disadvantages which require improvement.

(1) In order to produce the U-shaped double vertical tube/single capillary tube, more than 10 kinds of components and an entire manual assembly process for each component are required, so the assembly process is complicated and the production cost is high.

(2) In order to maintain a 36.5° C. environment similar to that of the human body, the tube has a sealed structure to be preheated and to maintain the temperature. Thus, it is impossible to monitor the movement situation of the blood sample in the U-tube, and it is impossible to recognize an error during the measurement.

(3) The size of the U-shaped double vertical tube/single capillary tube is large, so it takes a long time to preheat the tube to 36.5° C. which is similar to the human body temperature before the measurement.

(4) In order to measure the whole blood viscosity, a large amount of whole blood of 3.0 mL is required, so the blood collection burden is increased.

(5) The size of the U-shaped double vertical tube/single capillary tube is large and the structure thereof is complicated, so it is impossible to apply the tube to an automated inspection machine.

Therefore, there is a need for a development of a blood viscosity measurement kit in which the problems described above are improved.

SUMMARY OF INVENTION

Technical Problem

In order to solve the above problems, an object of the present invention is to provide a small blood viscosity measurement kit and a cartridge thereof in which a manufacturing process is simple, the manufacturing cost is low, and it is easy to be used in an automated device for blood viscosity measurement by miniaturizing and integrating the structure, to solve limitations of an existing blood viscosity measurement device used for the blood viscosity measurement.

Solution to Problem

In order to solve the problems described above, according to an embodiment of the present invention, there is provided a small blood viscosity measurement kit that is configured to measure a blood viscosity, including: a kit body; blood pipes disposed at both sides of the kit body which are formed symmetrically on both sides of the kit body, and of which an upper side is formed to be open so that blood is injected thereinto; and a fine channel connected to a lower side of the blood pipes. When blood is injected into one of the blood pipes disposed at both sides of the kit body, the blood is supplied to the other of the blood pipes through the fine channel.

Here, the fine channel has a length in a left-right direction and is formed to be curved.

In addition, the fine channel includes a first curved portion formed to be curved forward, and a second curved portion formed to be curved backward. The first curved portion and the second curved portion are alternately formed in a wavy shape in the left-right direction.

In addition, in small blood viscosity measurement kit, one or more of the total number of the first and second curved portions, a width of the first and second curved portions, and a distance of the fine channel are adjusted to adjust a flow resistance of the fine channel.

In addition, the fine channel is formed on a bottom surface of the kit body such that a lower surface is open, and the blood pipes disposed at both sides of the kit body are formed such that a lower surface is open. The small blood viscosity measurement kit may further include a fine channel cover that is mounted on the lower portion of the kit body to seal the open lower side of the blood pipes disposed at both sides of the kit body.

In addition, the fine channel cover may include a sealing protrusion that is formed to correspond to shapes of the fine channel and the blood pipes disposed at both sides of the kit body, and inserted into the fine channel and the blood pipes, and a coupling protrusion that is inserted into and coupled to the sealing protrusion and the kit body.

In addition, a height of the sealing protrusion is formed to be shorter than a depth of the fine channel.

In addition, the kit body may include a first coupling groove that is formed along an outer peripheral surface on a bottom surface so that the coupling protrusion is inserted thereinto, and one or more second coupling grooves that are formed adjacent to the first coupling groove and formed with an upper surface inclined downward from the outside to the inside so that the coupling protrusion is inserted thereinto.

In addition, the coupling protrusion may include a first coupling protrusion that is formed to protrude along an outer peripheral surface on an upper surface so as to be inserted into the first coupling groove, and a second coupling protrusion that is formed adjacent to the first coupling protrusion and formed with an upper surface inclined downward from the outside to the inside so as to be inserted into the second coupling groove.

In addition, a blood injection hole formed to penetrate from the upper surface to the lower surface may be provided, and an injection cover inserted into the upper side of the blood pipes disposed at both sides of the kit body may be provided.

In addition, blood injection hole may include an upper injection hole of which a diameter is formed to be gradually narrowed from an upper end to a lower end to be formed in an upper-wide and lower-narrow shape, and a lower injection hole of which a diameter is formed to be gradually narrowed from the lower end to the upper end to be formed in an upper-narrow and lower-wide shape.

In addition, the diameter of the lower injection hole is larger than that of the upper injection hole.

A small blood viscosity measurement kit cartridge, in which multiple small blood viscosity measurement kits are stored and kept, and the small blood viscosity measurement kit is able to be automatically supplied.

In addition, the small blood viscosity measurement kit cartridge may include: a cartridge body configured to store the multiple small blood viscosity measurement kits therein; a moving portion that is installed on one side of the cartridge body to move the small blood viscosity measuring kit to the other side; and a discharge portion that is installed on the other side of the cartridge body and is configured to export one small blood viscosity measurement kit to the outside of the cartridge body.

Advantageous Effects

According to an embodiment of the present invention, the small blood viscosity measurement kit and the cartridge thereof have advantages that a manufacturing process is simple by miniaturizing and integrating the structure, there is no need for a separate assembly process, and the manufacturing cost is low in order to solve the limitations of the existing blood viscosity measurement apparatus used for the blood viscosity measurement.

In addition, the transparent structure of which the inside is can be seen is provided, so that it is possible to monitor a situation of the movement of the blood sample from the outside in real time.

In addition, since the size of the kit is miniaturized, it is possible to quickly preheat the kit to 36.6° C. within a short time, and the sample required for blood viscosity measurement can be reduced to 1.0 mL or less, thereby reducing the burden of blood collection.

In addition, the small blood viscosity measurement kit and the cartridge thereof can be easily used in the automated device for the blood viscosity measurement.

BEST MODE FOR INVENTION

According to an embodiment of the present invention, there is provided a small blood viscosity measurement kit that is configured to measure a blood viscosity, including: a kit body; blood pipes disposed at both sides of the kit body which are formed symmetrically on both sides of the kit body, and of which an upper side is formed to be open so that blood is injected thereinto; and a fine channel connected to a lower side of the blood pipes. When blood is injected into one of the blood pipes disposed at both sides of the kit body, the blood is supplied to the other of the both blood pipes through the fine channel.

In addition, according to another embodiment of the present invention, there is provided a small blood viscosity measurement kit cartridge, in which multiple small blood viscosity measurement kits are stored and kept, and the small blood viscosity measurement kit is able to be automatically supplied.

MODE OF DISCLOSURE

Hereinafter, the description of the present invention with reference to the drawings is not limited to specific embodiments, and various modifications may be made and various embodiments may be provided. In addition, it should be understood that the contents described below include all transformations, equivalents, and substitutes included in the spirit and scope of the present invention.

In the following description, terms such as first, second, and the like are terms used to describe various configuration elements, are not limited in meaning to themselves, and are used only for the purpose of distinguishing one configuration element from other configuration elements.

Like reference numbers used throughout this specification refer to like elements.

As used herein, the singular expression includes the plural expression unless the context clearly dictates otherwise. In addition, terms such as "include", "provide" or "have" described below are intended to designate that the features, numbers, steps, operations, configuration elements, components, or combinations thereof described in the specification exist. It should be understood that this does not preclude a possibility of addition or existence of one or more other features, numbers, steps, operations, configuration elements, components, or combinations thereof.

Hereinafter, embodiments of the present invention will be described in detail with reference to the accompanying FIGS. 1 to 11.

Figure 1:
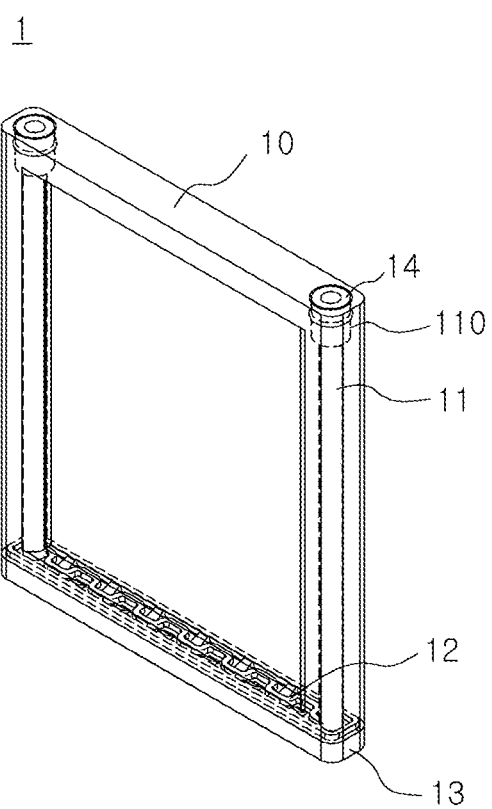
FIG. 1 is a perspective view illustrating a small blood viscosity measurement kit according to an embodiment of the present invention.
Figure 2:
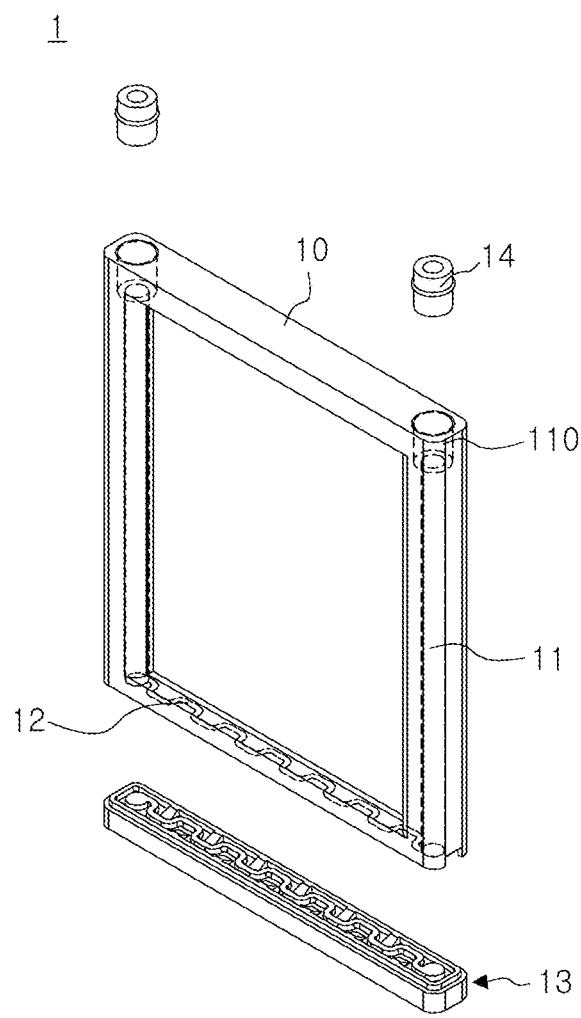
FIG. 2 is an exploded perspective view illustrating the small blood viscosity measuring kit according to the embodiment of the present invention.
Figure 3A:
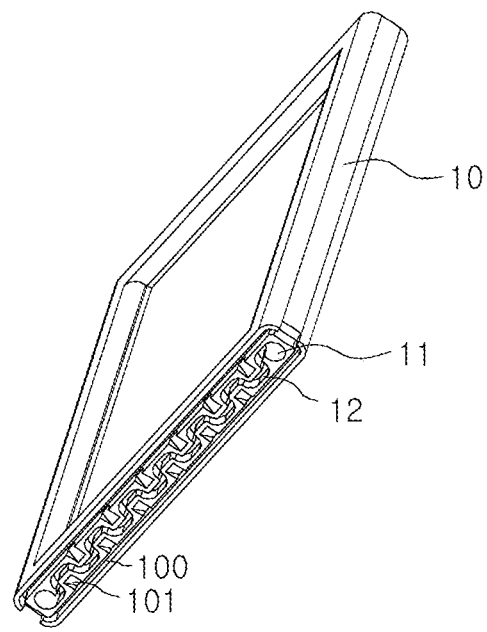
FIGS. 3A and 3B are a bottom perspective view and a bottom view illustrating a fine channel formed in a kit body of FIG. 2.
Figure 3B:
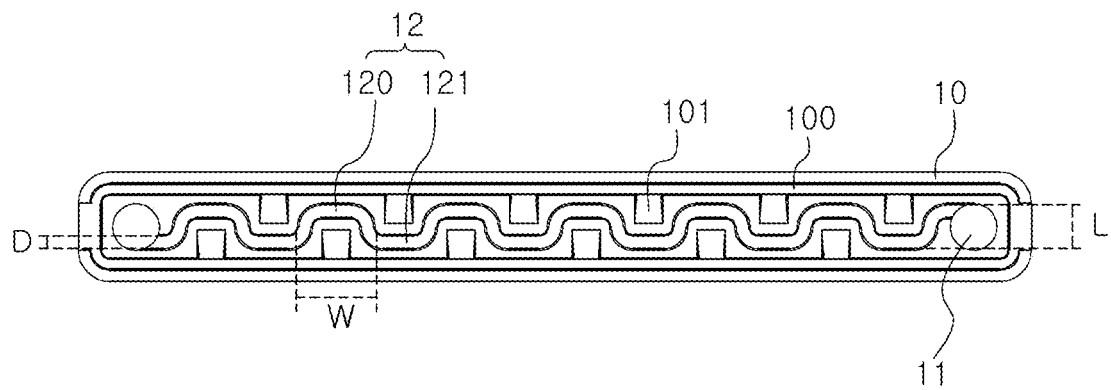
Figure 4:
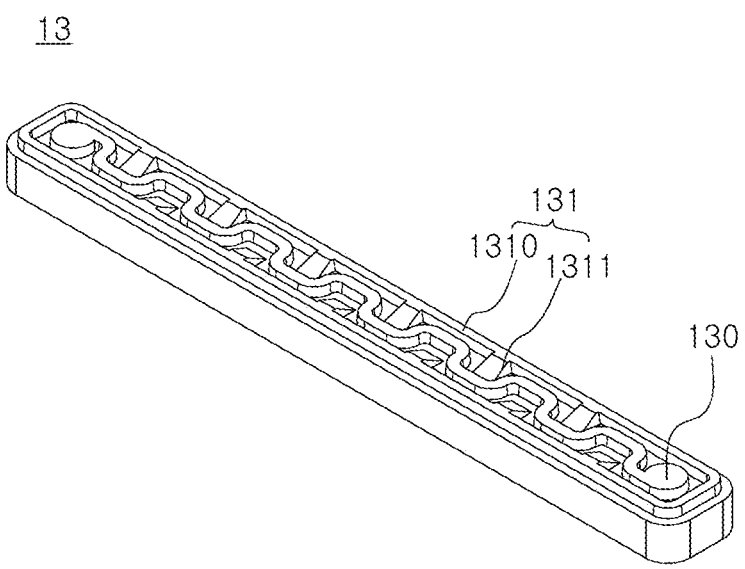
FIG. 4 is a perspective view illustrating a fine channel cover of FIG. 2.
Figure 5:
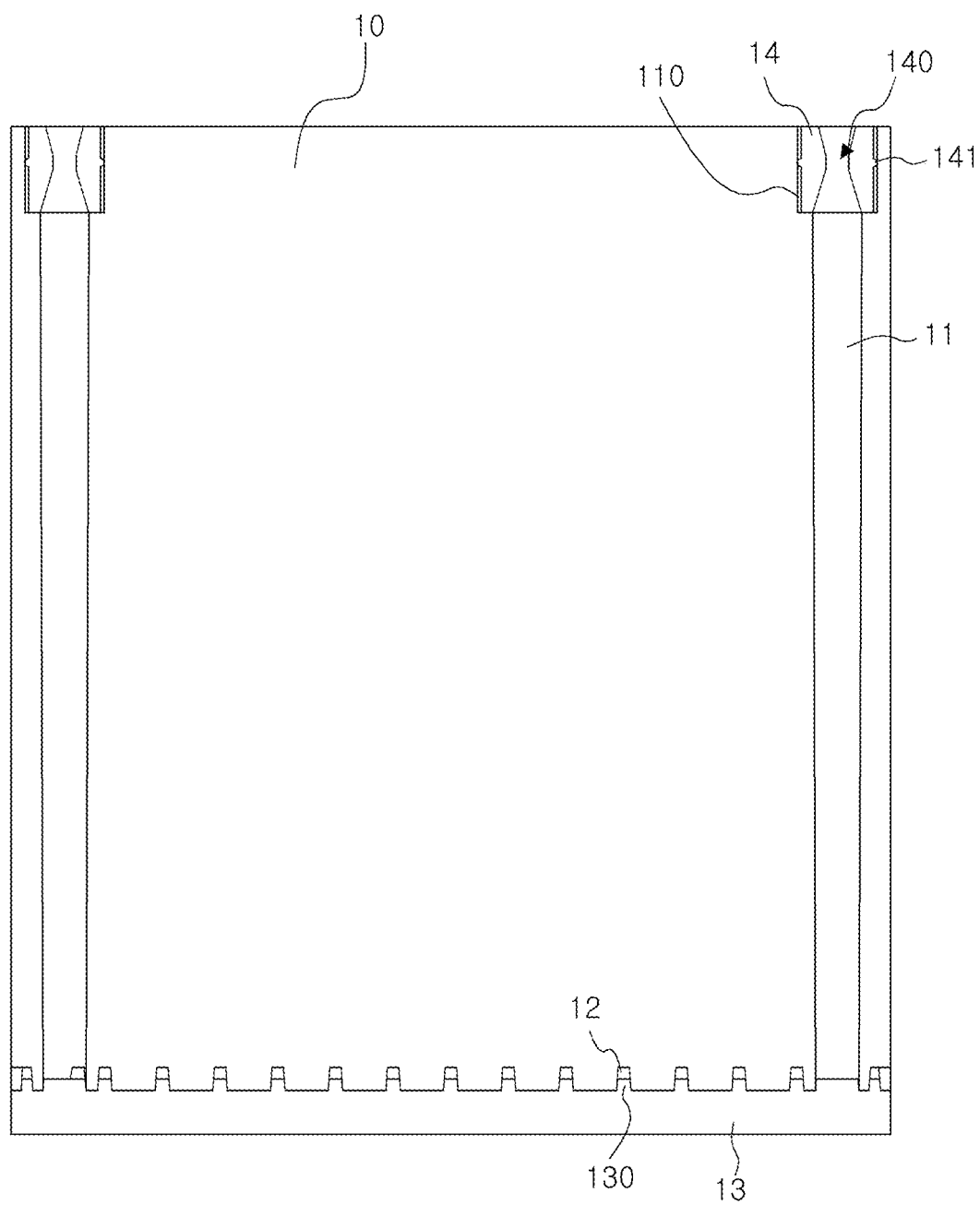
FIG. 5 is a front sectional view illustrating the small blood viscosity measurement kit of FIG. 1.
Figure 6A:
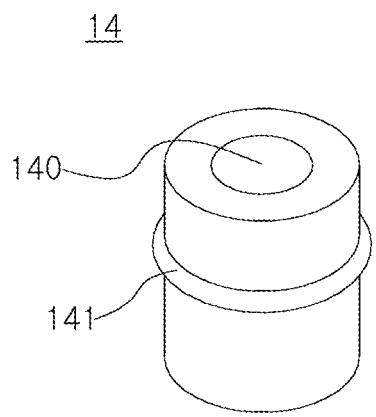
FIGS. 6A and 6B are a perspective view and a sectional view illustrating an injection cover of FIG. 2.
Figure 6B:
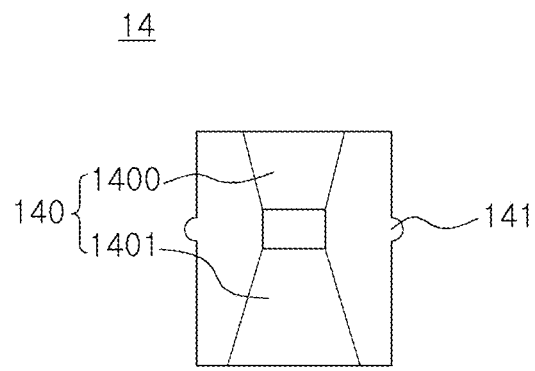

FIG. 1 is a perspective view illustrating a small blood viscosity measurement kit according to an embodiment of the present invention, FIG. 2 is an exploded perspective view illustrating the small blood viscosity measuring kit according to the embodiment of the present invention, FIGS. 3a and 3b are a bottom perspective view and a bottom view illustrating a fine channel formed in a kit body of FIG. 2, FIG. 4 is a perspective view illustrating a fine channel cover of FIG. 2, FIG. 5 is a front sectional view illustrating the small blood viscosity measurement kit of FIG. 1, and FIGS. 6a and 6b are a perspective view and a sectional view illustrating an injection cover of FIG. 2.

Referring to FIGS. 1 and 2, a small blood viscosity measurement kit 1 according to an embodiment of the present invention may include a kit body 10, blood pipes 11 disposed at both sides of the kit body 10, a fine channel 12 and a fine channel cover 13, and injection covers 14.

The kit body 10 may be formed of a transparent material, and blood pipes 11 disposed at both sides of the kit body 10 and fine channels 12 may be formed to allow blood to flow. As described above, it has a structure in which the inside is transparent, so that it is possible to check in real time a situation in which blood moves in the blood pipes 11 disposed at both sides of the kit body 10 and the fine channels 12.

Accordingly, it is possible to recognize an error during the blood viscosity measurement.

In addition, the kit body 10 is formed having a width within about 60 mm and a height within 70 mm, thereby being preferably formed in a compact size. This can reduce an amount of blood required for the blood viscosity measurement, and since it is necessary to preheat the kit to 36.5° C. to create an environment similar to the human body when performing the injection of blood, the preheating can be done quickly.

In addition, the kit body 10 may include a first coupling groove 100 and a second coupling groove 101 such that the fine channel cover 13 is coupled and fixed.

The first coupling groove 100 is formed along an outer peripheral surface on a bottom surface of the kit body 10 so that a first coupling protrusion 1310 may be inserted thereinto.

The multiple second coupling grooves 101 are formed adjacent to the first coupling groove 100, in a zigzag manner, in front and rear sides in a longitudinal direction, so that second coupling protrusions 1311 can be inserted thereinto. That is, the second coupling grooves 101 may be formed to be located between the first curved portions 120 and between the second curved portions 121.

In addition, the second coupling groove 101 may be formed with an upper surface inclined downward from the outside to the inside.

The blood pipes 11 disposed at both sides of the kit body 10 are formed symmetrically on both sides of the kit body 10, and the upper side is formed to be open, so that blood can be injected. Here, the blood pipes 11 disposed at both sides of the kit body 10 may be formed to have a length perpendicular to the upper surface of the kit body 10 when viewed from the front, but is not limited thereto, and may be formed to be inclined downward from both sides of the upper end of the kit body 10 toward the center.

In addition, the blood pipes 11 disposed at both sides of the kit body 10 may be formed to have an open lower surface, such that the open lower surface can be sealed by the fine channel cover 13. Accordingly, the blood injected into the blood pipes 11 disposed at both sides of the kit body 10 may flow into the fine channel 12 without being discharged to the outside.

In addition, the blood pipes 11 disposed at both sides of the kit body 10 may include cover insertion grooves 110 into which the injection cover 14 can be inserted, at the upper end.

The cover insertion grooves 110 are formed to be larger than the diameter of the blood pipes 11 disposed at both sides of the kit body 10 at the upper end of the blood pipes 11, and are formed to correspond to the size of the injection cover 14, so that the injection cover 14 can be inserted thereinto.

In addition, the lower ends of the blood pipes 11 disposed at both sides of the kit body 10 may be connected by the fine channel 12.

Accordingly, when blood is injected into one of the blood pipes 11 disposed at both sides of the kit body 10, blood may be supplied to the other of the blood pipes 11 through the fine channel 12.

The fine channel 12 may be connected to the lower sides of the two blood pipes 11 disposed at both sides of the kit body 10, respectively, to connect the two blood pipes 11.

The fine channel 12 connects the two blood pipes 11 disposed at both sides of the kit body 10 and has a length in the left-right direction so that blood can flow, and may be formed to be curved.

This is because, in a case where the fine channel 12 is formed in a straight line, due to a limitation of not being able to generate an appropriate flow resistance, when blood heights in the blood pipes 11 disposed at both sides of the kit body 10 become equal to each other, fluctuation may occur in the blood, so that the fine channel 12 is formed to be curved to freely form the flow resistance to a desired size and to prevent fluctuation therein from occurring.

Specifically, as illustrated in FIG. 3, the fine channel 12 includes the first curved portion 120 formed to be curved forward and the second curved portion 121 formed to be curved backward, and the first curved portion 120 and the second curved portion 121 may be alternately formed in a wavy shape in the left-right direction.

In this case, the first curved portion 120 and the second curved portion 121 are preferably formed in a symmetrical shape, and may be formed to be curved in various shapes such as a 'U' shape, a semicircle, a 'C' shape, and a 'V' shape.

By forming the fine channel 12 in this way, the fluctuation of the flow is minimized and the flow resistance of the fine channel 12 is easily adjusted so that when the blood heights in the blood pipes 11 disposed at both sides of the kit body 10 are equal to each other, the blood heights can be adjusted at a desired flow rate.

On the other hand, when the amount of blood for measuring the viscosity is small, the flow resistance is decreased to increase the flow rate. On the other hand, when the amount of blood is increased, the flow resistance is increased to decrease the flow rate to always maintain a constant flow rate to measure a constant blood viscosity. Therefore, it can be said that the adjustment of the flow resistance of the fine channel 12 is very important.

Conventionally, in order to adjust the flow rate, a method of adjusting the flow resistance by decreasing the size of the channel or making the inside of the channel rougher has been used, but these methods have a limit in the adjustment of the flow resistance to a desired size.

However, in the present invention, since the fine channel 12 is formed with the structure as described above, one or more of the total number of the first and second curved portions, a width W of the first and second curved portions, and a distance L of the fine channel are adjusted, and thereby the flow resistance of the fine channel 12 can be easily adjusted according to a desired requirement.

For example, the flow rate can be adjusted to be slow or fast by increasing the total number of first and second curved portions to increase the flow resistance or decreasing the total number of first and second curved portions to decrease the flow resistance.

In addition, the size D of the fine channel 12 may be at least 0.8 mm or more. This is because blood contains red blood cells, white blood cells, and platelets mixed with the plasma component such as water, and in a case where the size D of the fine channel 12 is formed of less than 0.8 mm, red blood cells, white blood cells, platelets, and the like are collected only in the center of the fine channel 12, so that the frictional resistance caused by the cells is ignored and accurate blood viscosity cannot be measured.

The fine channel 12 is preferably formed on the bottom surface of the kit body 10 so as to form the lower surface thereof to be open. In this case, the open lower side of the fine channel 12 may be sealed by the fine channel cover 13.

This can facilitate the fabrication of the curved fine channel 12 and allow the fine channel 12 to be opened by separation of the fine channel cover 13 to facilitate cleaning and disinfection after use. Alternatively, the blood can be easily washed away and then the kit body can be thrown away even at the time of disposal, so it can be kept clean.

The fine channel cover 13 may be mounted on the lower portion of the kit body 10 to seal the fine channel 12 and the open lower sides of the blood pipes 11 disposed at both sides of the kit body 10.

The fine channel cover 13 may include a sealing protrusion 130 and a coupling protrusion 131 as illustrated in FIG. 4.

The sealing protrusion 130 is formed to correspond to the shape of the fine channel 12 and the blood pipes 11 disposed at both sides of the kit body 10, and may be inserted into the lower side of the fine channel 12 and the blood pipes 11.

In addition, the sealing protrusion 130 is formed to have a height shorter than a depth of the fine channel 12, so that, when being coupled, there is a separation space as illustrated in FIG. 5. Therefore, the blood injected into the blood pipes 11 disposed at both sides of the kit body 10 can flow along the fine channel 12.

The coupling protrusion 131 may be inserted into and coupled to the first coupling groove 100 and the second coupling groove 101 of the kit body 10.

Specifically, the coupling protrusion 131 may include a first coupling protrusion 1310 and a second coupling protrusion 1311.

The first coupling protrusion 1310 may be formed to protrude upward along the outer peripheral surface on the upper surface of the fine channel cover 13. Accordingly, the first coupling protrusion 1310 is inserted into the first coupling groove 100 of the kit body 10 so that the kit body 10 and the fine channel cover 13 may be coupled to each other.

The second coupling protrusion 1311 is provided for making the coupling between the fine channel cover 13 and the kit body 10 more robust, and is formed adjacent to the first coupling protrusion 1310. The multiple second coupling protrusions 1311 are formed, in a zigzag manner, in the front and rear sides in the longitudinal direction and may be inserted into the second coupling grooves 101.

In addition, the second coupling protrusion 1311 may have an upper surface inclined downward from the outside to the inside. Accordingly, as the second coupling protrusion 1311 is inserted into the second coupling groove 101, a coupling force is improved, and the fine channel cover 13 can be easily separated during separation.

The injection covers 14 are inserted into the cover insertion grooves 110 formed on the upper side of the blood pipes 11 disposed at both sides of the kit body 10, so that when blood is injected into the blood pipes 11 with a pipette, external air is not injected together with the blood and it is possible to prevent formation of air bubbles in the blood. Accordingly, it is possible to prevent the flow of blood from being disturbed by the air bubbles generated in the blood.

The injection cover 14 may include a blood injection hole 140 and a friction protrusion 141.

Referring to FIG. 6, the blood injection hole 140 may be formed to penetrate from the upper surface to the lower surface of the injection cover 14, and may include an upper injection hole 1400 and a lower injection hole 1401.

The upper injection hole 1400 is formed on the upper side of the injection cover 14, and a diameter thereof may be gradually narrowed from the upper end to the lower end to be formed in an upper-wide and lower-narrow shape. Accordingly, when blood is injected with the pipette, an inclined structure of the pipette and the upper injection hole 1400 are exactly matched, so that blood can be injected in a state where the pipette and the upper injection hole 1400 are in close contact with each other. Therefore, it is possible to prevent external air from being introduced into the upper injection hole 1400 the together with the blood.

The lower injection hole 1401 is formed on the lower side of the injection cover 14, and a diameter thereof is gradually narrowed from the lower end to the upper end to be formed in an upper-narrow and lower-wide shape.

The lower injection hole 1401 may be directly connected to the upper injection hole 1400, or may also be connected thereto via an intermediate injection hole. The intermediate injection hole is formed with a uniform diameter from the upper end to the lower end to connect the lower injection hole 1401 and the upper injection hole 1400. In this case, the tip of the inclined structure of the pipette is allowed to be in close contact with the upper injection hole 1400. Therefore, it is possible to more effectively block the introduction of external air.

In addition, the lower injection hole 1401 may be formed such that the diameter thereof is formed greater than that of the upper injection hole 1400.

The lower injection hole 1401 is formed as described above such that when external air is introduced through the pipette, even if a little of external air is introduced together, the introduced air may stay in the lower injection hole 1401 without entering the fine channel 12 along with the blood.

Accordingly, it is possible to effectively prevent the formation of air bubbles in the blood.

The friction protrusion 141 is formed to protrude along the outer peripheral surface of the injection cover 14, and when the injection cover 14 is inserted into the cover insertion groove 110, the fixing thereof becomes more robust by friction and introduction of external air can be prevented.

A small blood viscosity measurement kit cartridge 2, which is capable of storing multiple small blood viscosity measurement kits 1 formed as described above and automatically supplying the stored small blood viscosity measurement kit 1, will be described in detail below.

Figure 7:
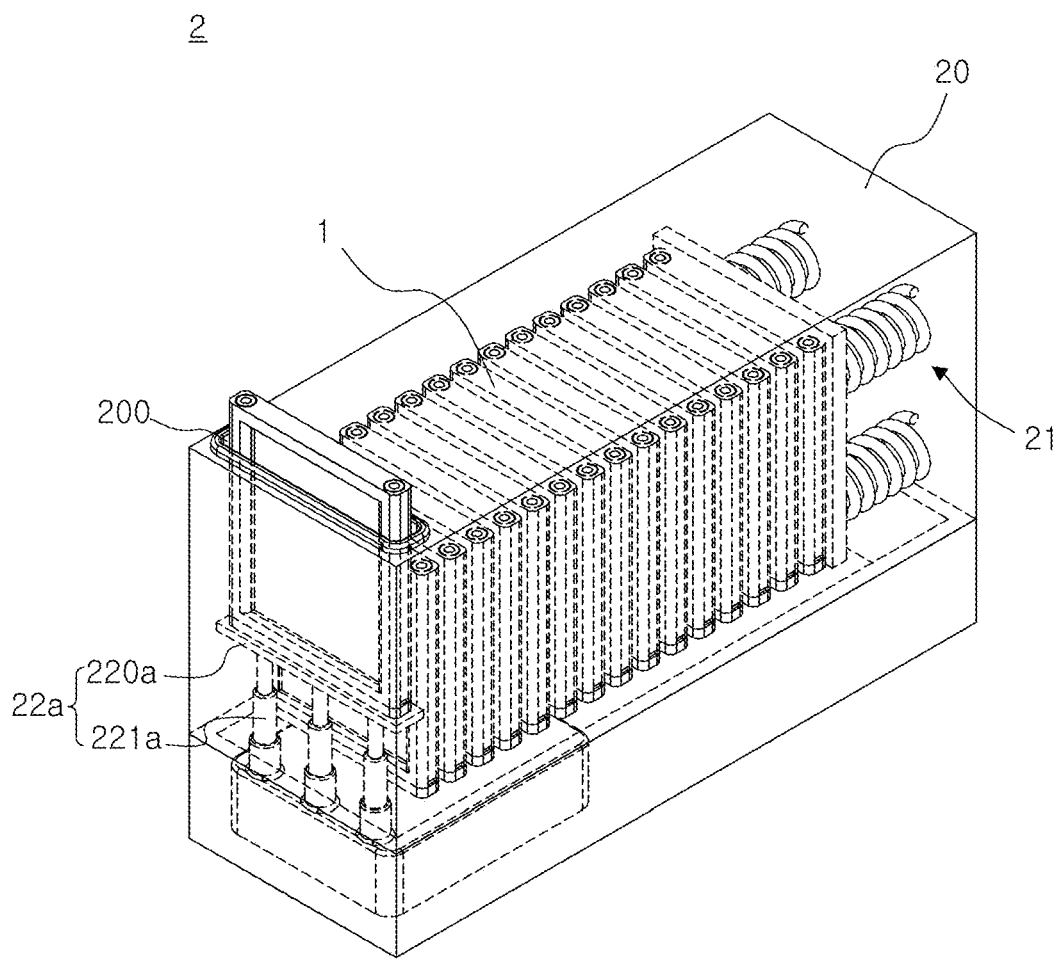
FIG. 7 is a perspective view illustrating a small blood viscosity measurement kit cartridge according to a first embodiment of the present invention.

FIG. 7 is a perspective view illustrating a small blood viscosity measurement kit cartridge according to a first embodiment of the present invention.

Referring to FIG. 7, the small blood viscosity measurement kit cartridge 2 according to the first embodiment of the present invention may include a cartridge body 20, a moving portion 21 and a discharging portion 22a.

First, the cartridge body 20 is capable of storing the multiple small blood viscosity measurement kits 1 therein, and may be formed in an empty box shape, but is not limited thereto.

In addition, the cartridge body 20 includes a discharge hole 200 such that the small blood viscosity measurement kit 1 can be pulled out therefrom, and may include a door such that the inside thereof can be filled with the small blood viscosity measurement kits 1.

The discharge hole 200 is formed in the upper surface of the cartridge body 20 on one side and can discharge the small blood viscosity measurement kit 1 inside the cartridge body 20.

The door is formed on the other side of the cartridge body 20 such that the cartridge body 20 can be opened and sealed. Accordingly, the cartridge body 20 can be easily filled with the small blood viscosity measurement kits 1.

The moving portion 21 is installed on one side inside the cartridge body 20 to move the small blood viscosity measuring kit 1 to the other side.

To this end, the moving portion 21 may be formed of an elastic member, but is not limited thereto, and may be provided as a cylinder or the like.

In a case of being formed of the elastic member, an elastic force is given to the small blood viscosity measurement kit 1, and when a space is formed as the small blood viscosity measurement kit 1 exits, the small blood viscosity measurement kit 1 can be moved to the other side by the elastic force.

In a case of being provided as the cylinder, the small blood viscosity measurement kit 1 can be moved to the other side by taking out.

The discharge portion 22a is installed on the other side of the cartridge body 20 and can export the small blood viscosity measurement kit 1 located at the outermost end of the cartridge body 20 to the outside so as to be removed from the cartridge body 20.

The discharge portion 22a may include a lifting plate 220a and a lifting cylinder 221a.

The lifting plate 220a is formed in a square plate shape and can be lifted and lowered by the lifting cylinder 221a, and can lift and lower the small blood viscosity measuring kit 1 placed on the upper side thereof as the lifting plate 220a is lifted and lowered.

In addition, the small blood viscosity measurement kit cartridge 2 may further include a control unit (not illustrated).

The control unit (not illustrated) controls the moving portion 21 and the discharge portion 22a, respectively, so that the small blood viscosity measurement kit 1 can be pulled out from the cartridge body 20.

The control unit (not illustrated) is installed in the discharge portion 22a and can control the moving portion 21 and the discharge portion 22a according to whether there is the small blood viscosity measurement kit 1 on the upper side of the discharge portion 22a, from a sensor unit (not illustrated) that detects the small blood viscosity measurement kit 1.

Figure 8:
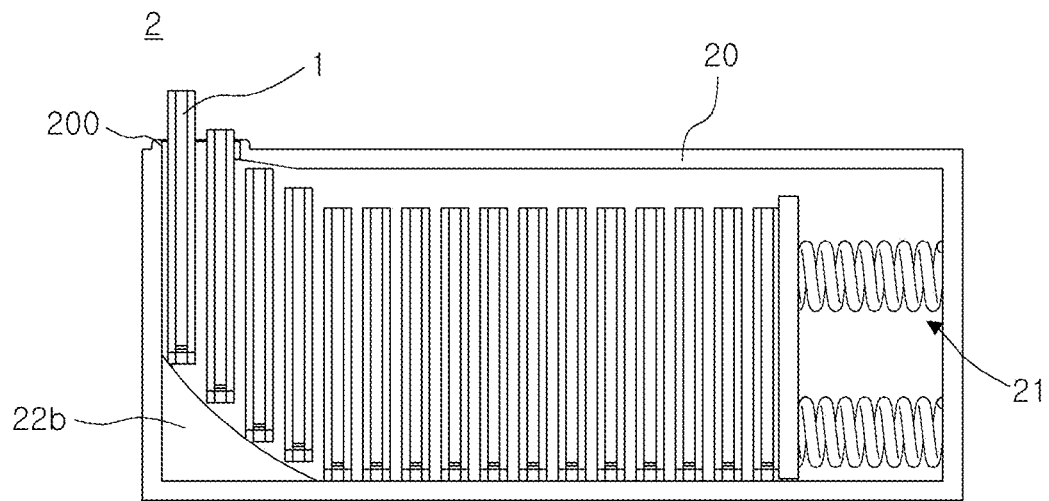
FIG. 8 is a side sectional view illustrating a small blood viscosity measurement kit cartridge according to a second embodiment of the present invention.

FIG. 8 is a side sectional view illustrating a small blood viscosity measurement kit cartridge according to a second embodiment of the present invention.

Referring to FIG. 8, a small blood viscosity measurement kit cartridge 2 according to the second embodiment of the present invention may be formed with a discharge portion 22b in a form different from that of the first embodiment.

Here, the small blood viscosity measurement kit cartridge 2 according to the second embodiment of the present invention is practically the same as the small blood viscosity measurement kit cartridge 2 according to the first embodiment of the present invention described above except for the discharge portion 22b.

Therefore, only the discharge portion 22b will be described.

The discharge portion 22b may be formed of an inclined surface inclined downwardly from the front to the lower surface inside the cartridge body 20.

Accordingly, when being transferred to the other side by the moving portion 21, the small blood viscosity measurement kit 1 moves upward along the inclined surface of the discharge portion 22b, and the small blood viscosity measurement kit 1 can be discharged through the discharge hole 200.

Figure 9A:
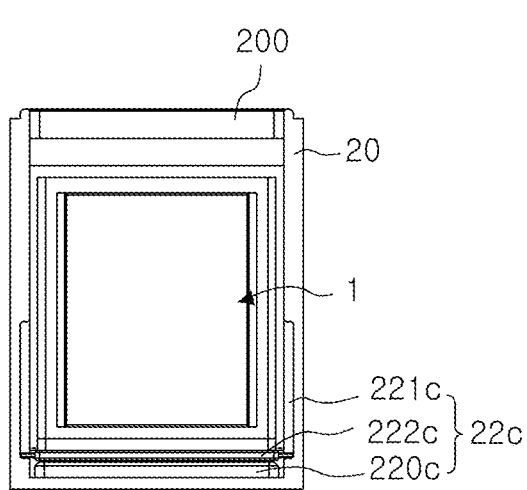
FIGS. 9A and 9B are exemplary views illustrating an operation state of a discharge portion of a small blood viscosity measurement kit cartridge according to a third embodiment of the present invention.
Figure 9B:
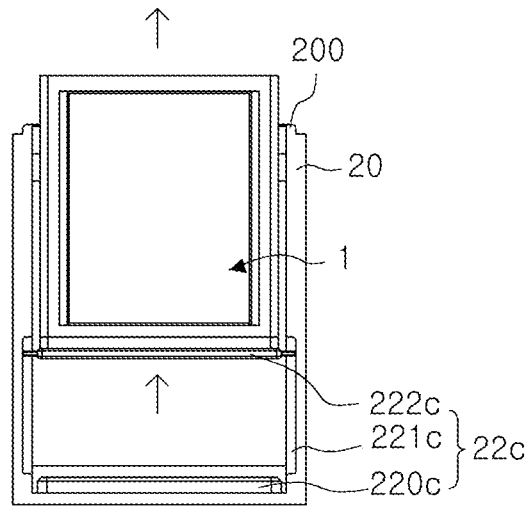

FIGS. 9a and 9b are exemplary views illustrating an operation state of a discharge portion of a small blood viscosity measurement kit cartridge according to a third embodiment of the present invention.

Referring to FIG. 9, the small blood viscosity measurement kit cartridge 2 according to the third embodiment of the present invention may be formed with a discharge portion 22c in a form different from that of the first embodiment.

Here, the small blood viscosity measurement kit cartridge 2 according to the third embodiment of the present invention is practically the same as the small blood viscosity measurement kit cartridge 2 according to the first embodiment of the present invention described above except for the discharge portion 22c.

Therefore, only the discharge portion 22c will be described.

The discharge portion 22c may include an electromagnet 220c, a guide portion 221c, and a magnet plate 222c.

The electromagnet 220c may be formed on the other side of the lower surface of the cartridge body 20. When electricity flows by a control unit (not illustrated), the electromagnet 220c is magnetized, and when electricity is cut off, the electromagnet 220c can return to an unmagnetized original state. Accordingly, when the electromagnet 220c is magnetized, the magnet plate 222c installed on the upper side thereof can be pushed upward, and when the electromagnet 220c is not magnetized, the magnet plate 222c can also be returned to its original position.

The guide portions 221c are formed on both sides of the cartridge body 20 in the up-down direction, respectively, so that the magnet plate 222c can move up and down along the guide portions 221c. That is, guide protrusions of the magnet plate 222c are inserted into the guide portions 221c to move along the guide portions 221c.

The magnet plate 222c may include the guide protrusions that are installed on the electromagnet 220c and are coupled to the guide portions 221c at both ends. The magnet plate 222c is pushed upward by the magnetized electromagnet 220c and can move upward the small blood viscosity measurement kit 1 located on the upper side, and when the electromagnet 220c returns to its original state without being magnetized, the magnet plate 222c can go back down.

Figure 10:
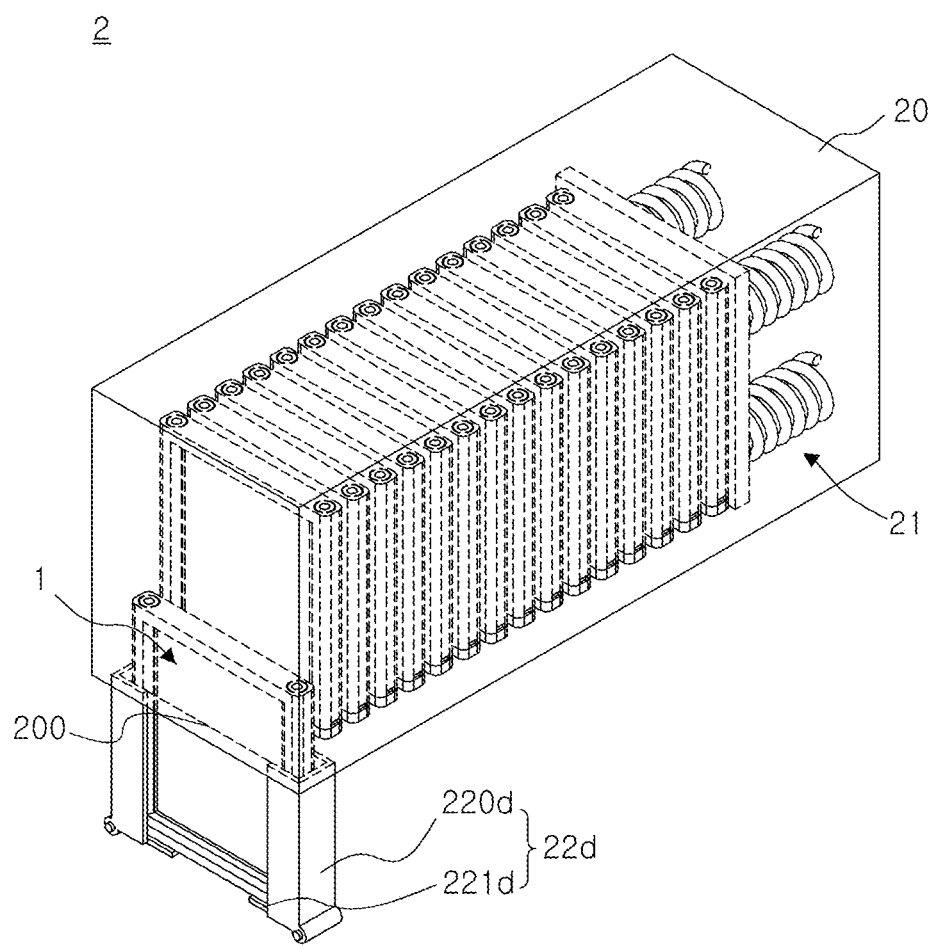
FIG. 10 is a perspective view illustrating a small blood viscosity measurement kit cartridge according to a fourth embodiment of the present invention.
Figure 11A:
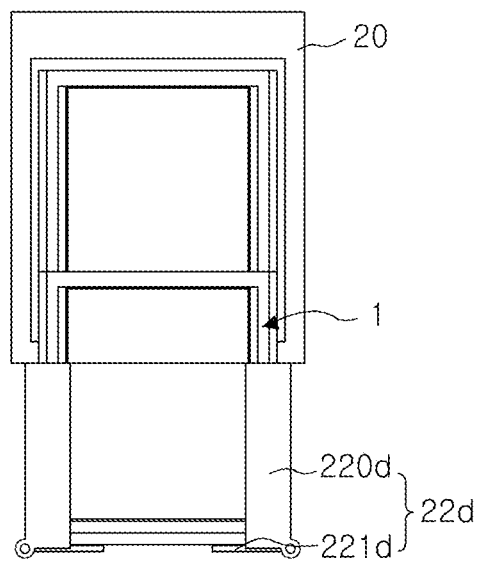
FIGS. 11A and 11B are exemplary views illustrating an operation state of a discharge portion of the small blood viscosity measurement kit cartridge according to the fourth embodiment.
Figure 11B:
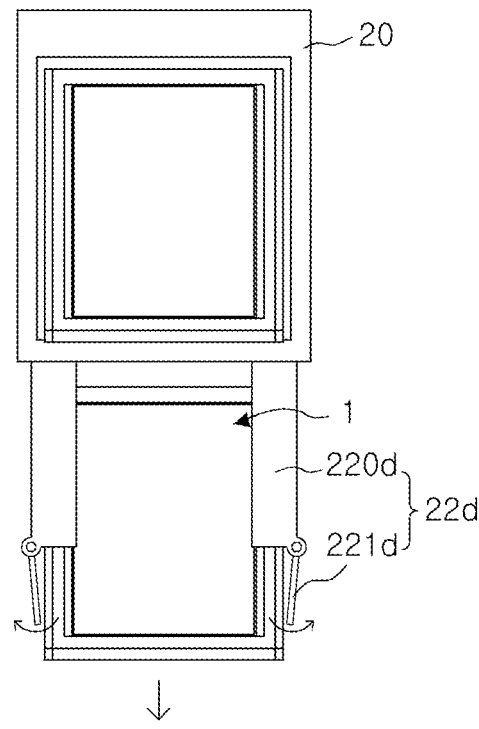

FIG. 10 is a perspective view illustrating a small blood viscosity measurement kit cartridge according to a fourth embodiment of the present invention, and FIGS. 11a and 11b are exemplary views illustrating an operation state of a discharge portion of the small blood viscosity measurement kit cartridge according to the fourth embodiment.

Referring to FIGS. 10 and 11, a small blood viscosity measurement kit cartridge 2 according to the fourth embodiment of the present invention may be formed with a discharge portion 22d in a form different from that of the first embodiment.

Here, the small blood viscosity measurement kit cartridge 2 according to the fourth embodiment of the present invention is practically the same as the small blood viscosity measurement kit cartridge 2 according to the first embodiment of the present invention described above except for the discharge portion 22d and a position of the discharge hole 200.

Therefore, only the discharge portion 22d and the discharge hole 200 will be described.

Here, the discharge hole 200 may be formed on the lower surface of the cartridge body 20 on the other side. Accordingly, when the small blood viscosity measurement kit 1 is pushed to the other side by the moving portion 21, the small blood viscosity measurement kit 1 located at the outermost end can be directly pulled out into the discharge hole 200.

The discharge portion 22d may include a guide plate 220d and a support plate 221d.

The guide plates 220d are formed vertically downward on both sides of the lower surface of the cartridge body 20, and may be formed on both sides where the discharge hole 200 is formed.

In this case, the guide plate 220d is formed in a 'C' shape in cross section when viewed from the upper surface, so that the small blood viscosity measuring kit 1 being pulled out to the discharge hole 200 can be lowered along the guide plates 220d.

The support plate 221d is rotatably connected to a lower end of the guide plate 220d to support the small blood viscosity measurement kit 1 coming down along the guide plate 220d so as not to be fallen. Thereafter, if a user wants to use the small blood viscosity measurement kit 1, the support plate 221d is rotated by pulling the small blood viscosity measurement kit 1 downward, so that the small blood viscosity measurement kit 1 can be pulled out therefrom.

As described above, the small blood viscosity measurement kit and the cartridge thereof according to the embodiment of the present invention as described above have advantages that a manufacturing process is simple by miniaturizing and integrating the structure, there is no need for a separate assembly process, and the manufacturing cost is low in order to solve the limitations of the existing blood viscosity measurement apparatus used for the blood viscosity measurement.

In addition, the transparent structure of which the inside is can be seen is provided, so that it is possible to monitor a situation of the movement of the blood sample from the outside in real time.

In addition, since the size of the kit is miniaturized, it is possible to quickly preheat the kit to 36.6° C. within a short time, and the sample required for blood viscosity measurement can be reduced to 1.0 mL or less, thereby reducing the burden of blood collection.

In addition, the small blood viscosity measurement kit and the cartridge thereof can be easily used in the automated device for the blood viscosity measurement.

In the above, the small blood viscosity measurement kit cartridges according to the embodiments of the present invention have been described by dividing them into the first to fourth embodiments. However, the present invention has been described by dividing the embodiments for convenience and easy understanding of the description, and is not limited to each embodiment, and the configurations of the embodiments may be applied to each other by changing the design.

Although the embodiments of the present invention have been described above with reference to the accompanying drawings, it will be able to understand that those of ordinary skill in the art to which the present invention pertains can practice the present invention in other specific forms without changing the technical spirit or essential features of the present invention. Accordingly, the embodiments described above are illustrative in all respects and not restrictive.

The invention claimed is:

1. A small blood viscosity measurement kit comprising:
    a kit body;
    two blood pipes disposed symmetrically on two sides of the kit body;
    a fine channel connected to a lower side of each of the two blood pipes; and
    a fine channel cover detachably coupled to a lower part of the kit body configured to seal a lower surface of the fine channel and the lower side of the each of the two blood pipes,
    wherein an upper side of each of the two blood pipes is open and configured to receive blood injected thereinto,
    wherein when the blood is injected into one blood pipe of the two blood pipes, the blood is supplied to another blood pipe of the two blood pipes through the fine channel, and
    wherein the fine channel cover includes:
        a sealing protrusion configured to be inserted into the lower surface of the fine channel and the lower side of the each of the two blood pipes, and
        a coupling protrusion configured to be coupled to the kit body.

2. The small blood viscosity measurement kit of claim 1, wherein the fine channel is elongated in a horizontal direction and includes plurality of curved portions.

3. The small blood viscosity measurement kit of claim 2, wherein the fine channel comprises:
at least one first curved portion disposed to be curved forward; and
at least one second curved portion disposed to be curved backward, and
wherein the at least one first curved portion and the at least one second curved portion are alternately disposed in a wavy shape in the horizontal direction.

4. The small blood viscosity measurement kit of claim 3, wherein a total number of the at least one first curved portion and the at least one second curved portion, a width of the at least one first curved portion and the at least one second curved portion, and a total length of the fine channel are configured to be adjusted and control a flow resistance of the fine channel.

5. The small blood viscosity measurement kit of claim 1, wherein the fine channel is disposed on a bottom surface of the kit body and the lower surface of the fine channel is open, and
wherein the lower side of the each of the two blood pipes is open.

6. The small blood viscosity measurement kit of claim 1, further comprising:
an injection cover inserted into the upper side of the each of the two blood pipes, wherein the injection cover comprises a blood injection hole penetrating through an upper surface to a lower surface of the injection cover.

7. The small blood viscosity measurement kit of claim 6, wherein the blood injection hole comprises,
an upper injection hole having a diameter which gradually narrows from an upper end to a lower end thereof to be formed in an upper-wide and lower-narrow shape, and
a lower injection hole having a diameter which gradually narrows from a lower end to an upper end thereof to be formed in an upper-narrow and lower-wide shape.

8. The small blood viscosity measurement kit of claim 1, wherein the kit body further comprises:
a first coupling groove defined along an outer peripheral surface on a bottom surface of the kit body; and
at least one second coupling groove defined adjacent to the first coupling groove and having an upper surface inclined downward.

9. The small blood viscosity measurement kit of claim 8, wherein the sealing protrusion is configured to correspond to a shape of the fine channel and the each of the two blood pipes, and
wherein the coupling protrusion includes:
a first coupling protrusion configured to couple to the first coupling groove of the kit body, and
at least one second coupling protrusion configured to couple to the at least one second coupling groove of the kit body.

10. The small blood viscosity measurement kit of claim 1, wherein the sealing protrusion has a height shorter than a depth of the fine channel.

11. The small blood viscosity measurement kit of claim 9, wherein the first coupling protrusion protrudes upward along an outer peripheral surface on an upper surface of the fine channel cover, and
wherein the at least one second coupling protrusion is disposed adjacent to the first coupling portion and has an upper surface inclined downward.

12. The small blood viscosity measurement kit of claim 9, wherein the at least one second coupling protrusion includes a plurality of second coupling protrusions in a longitudinal direction.

\* \* \* \* \*